(12) United States Patent
Lin et al.

(10) Patent No.: US 6,598,485 B1
(45) Date of Patent: Jul. 29, 2003

(54) METHOD AND DEVICE FOR EVALUATING QUALITY OF CONCRETE STRUCTURES

(75) Inventors: Yiching Lin, Taichung (TW); Chiafeng Chang, Hsi-Chih (TW)

(73) Assignee: Sinotech Engineering Consultants, Inc., Taipei (TW)

( * ) Notice: Subject to any disclaimer, the term of this patent is extended or adjusted under 35 U.S.C. 154(b) by 113 days.

(21) Appl. No.: 09/722,098

(22) Filed: Nov. 24, 2000

(51) Int. Cl.[7] .............................. G01N 3/00; G01M 7/00
(52) U.S. Cl. ..................................... 73/803; 73/12.01
(58) Field of Search ........................ 73/82, 803, 12.01, 73/12.04, 12.07, 12.08, 12.09

(56) References Cited

U.S. PATENT DOCUMENTS

| | | | | | |
|---|---|---|---|---|---|
| 4,479,386 | A | * | 10/1984 | Beggs et al. | 73/579 |
| 4,702,111 | A | * | 10/1987 | Holland | 73/579 |
| 4,990,897 | A | * | 2/1991 | Beyma et al. | 340/323 R |
| 5,024,090 | A | * | 6/1991 | Pettigrew et al. | 73/572 |
| 5,804,707 | A | * | 9/1998 | Scarton et al. | 73/82 |
| 5,883,569 | A | * | 3/1999 | Kolefas | 273/372 |
| 5,983,701 | A | * | 11/1999 | Hassani et al. | 73/12.01 |
| 6,029,521 | A | * | 2/2000 | Lin et al. | 73/12.01 |

* cited by examiner

Primary Examiner—Max Noori
Assistant Examiner—Lilybett Martir

(57) ABSTRACT

An evaluation device and an evaluation method for detecting quality of concrete structures comprising a conductive impact device, a sensing film, a receiver, an operation device and an auxiliary circuit, the device and the method is characterized by calculating a penetration time of the conductive film before measuring the depth of a crack in the concrete, and the evaluation work which conventionally requires dual receivers only needs now a single receiver for completion of the work. Therefore, cost and works for evaluation and signal analysis are reduced; this largely enhances the evaluation efficiency and technical level.

4 Claims, 7 Drawing Sheets

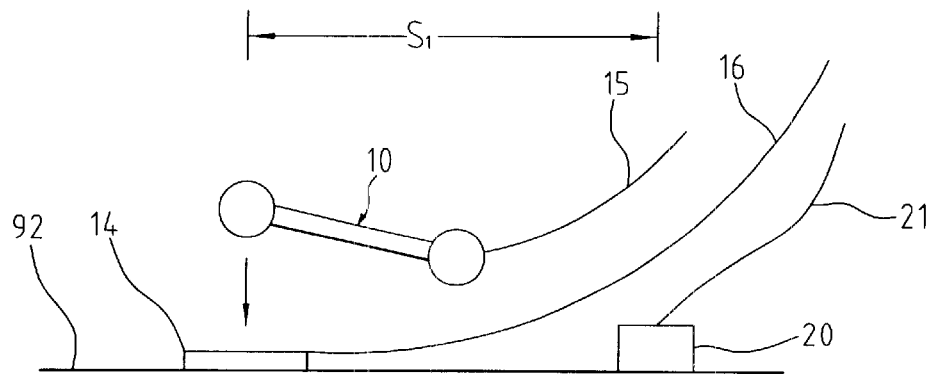
Fig.3A
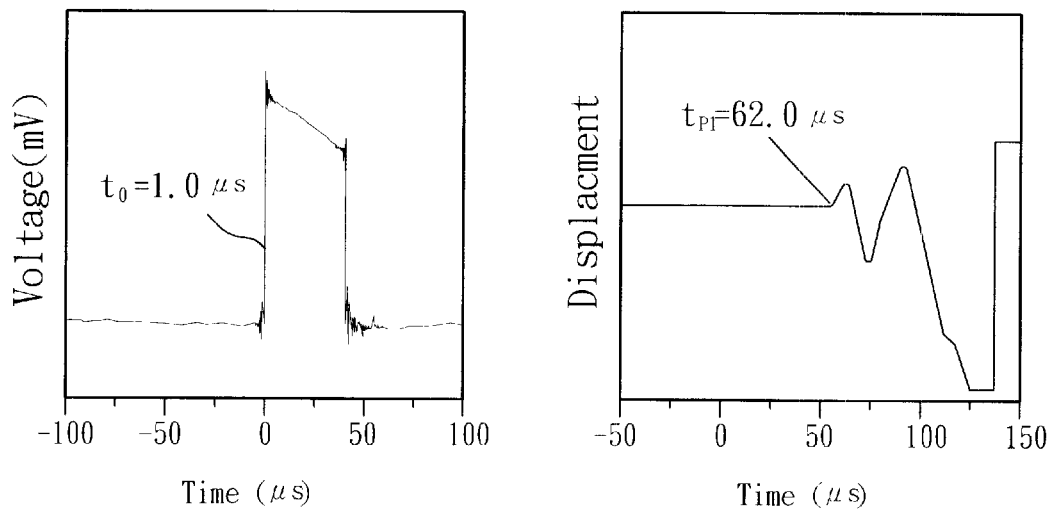
Fig.3B  Fig.3C

METHOD AND DEVICE FOR EVALUATING QUALITY OF CONCRETE STRUCTURES

BACKGROUND OF THE INVENTION

1. Field of the Invention

The present invention is related to a method and a device for evaluating quality of concrete structures. The device includes a sensing film able to detect the time when a source of waves is generated. With the device, stress waves are generated and the time that the source of waves is generated is recorded. So that the evaluation work which conventionally requires dual receivers only needs a single receiver for completion of the work.

2. Description of the Prior Art

Conventionally, nondestructive testing techniques for concrete have been developed, wherein, an impact-echo method developed in the middle of 1980 generates stress waves in concrete by impact; the degree of the impact force and the size of the device for impact can be adjusted to control the desired energy and frequency of the stress waves. The impact-echo method uses a signal receiver which is made of inverted conical piezo-electric material, the device makes a point contact with concrete, so that the surface of the concrete needs no grinding for flattening. Application of the impact-echo method in measuring the thickness of concrete plates has been included in the ASTM as a standard test method in 1998.

A time-of-flight diffraction technique for detecting the depth of a surface-opening crack in concrete uses steel spheres as impact sources. After impact on the concrete, longitudinal waves (P waves: pressure waves), transverse waves (S waves: shear waves) and Raleigh's waves (R waves: surface waves) are generated. Wherein, the P waves and S waves are propagated into concrete in the shape of a semi-sphere, while R waves are spread out from the impact point on the concrete surface in the shape of a circle. The source of the waves is generated at the moment when the sphere strikes the surface of the concrete; by virtue that the time when the sphere impacts the surface of the concrete to generate the source of the waves can not be obtained directly, an indirect way was used conventionally to determine the occurring time of the source of waves by locating a receiver close to the impact point. The principle of the indirect way for detecting the vertical depth of a surface-opening crack is as below:

The longitudinal waves (P waves) and the transverse waves (S waves) generated by impacting the surface of the concrete propagate inwardly of the concrete; the P waves go faster, hence the wavefront thereof meets the tip of the crack firstly, then the S waves arrive, the incident P waves generate diffraction waves at the tip of the crack to propagate in the shape of a sphere as a new source of waves generated at the tip of the crack. When the diffraction waves are transmitted back to the impacted surface of the concrete, disturbance is induced. To record the time for stress waves traveling from the impact point via the diffraction at the crack tip to arrival at the surface on the other side of the crack, two receivers sensitive to the vertical displacement of particles are respectively disposed at both sides of the surface-opening crack. The waveform of the displacement detected by the receiver at the same side as that of the position of impact is controlled mainly by a downward displacement created by the R waves; thereafter, the waveform is influenced by the disturbances caused by arrivals of the reflecting waves and the diffraction waves. The initial disturbance detected by the receiver at the different side from that of the position of impact is caused by the arrival of the P wave diffracted from the tip of the crack, because the crack that impedes and delays arrival of the R waves. And then, the displacement waveform detected is generated by the subsequent arrivals of the reflecting waves and the diffraction waves.

FIG. 1 is a schematic view showing evaluation and detection of the crack. A first receiver 93 is located at a distance HO from the source of impact 91, the distances between the source of impact 91 and the crack and between the crack and a second receiver 94 are respectively $H_1$ and $H_2$. When the first receiver 93 receives a downward displacement created by the R waves, the signal monitoring system is activated. We hereby provide that arrival time of the R waves is $t_1$, the time that the second receiver 94 records arrival of the diffraction waves going around the tip of the crack is $t_2$, and the time difference between sensing the arrival of the R waves by the first receiver 93 and sensing the arrival of the diffraction waves by the second receiver 94 is $t_2\ t_1$.

Impact is done before sensing the arrival of the R waves by the first receiver 93, thereby, the initial time of impact shall be obtained by derivation. And this is the propagation time of the R waves from the source of impact 91 to the first receiver 93, i.e., the value of $H_O$ divided by the speed of the R waves ($C_R$). Thereby, the time period of the P waves from the source of impact 91 to the second receiver 94 can be obtained from the following calculation formula:

$$\Delta t = t_2 - t_1 + \frac{H_o}{C_R} \tag{1}$$

The length of path that the P waves go along equals to the multiplication of the speed of the P waves ($C_P$) and the time taken, thereby, the depth (d) of the surface-opening crack in concrete is calculated according to the following formula:

$$d = \sqrt{\left[\frac{(C_P \times \Delta t)^2 + H_1^2 - H_2^2}{2 \times C_P \times \Delta t}\right]^2 - H_1^2} \tag{2}$$

Analysis of Difficulty Resided in the Prior Art

The prior art has five steps in detecting a crack, it is hereby stated as follows (referring to FIG.1):

Step 1 (measuring speed of the R waves $C_R$): The two receivers 93, 94 are allocated on the surface 92 of concrete and has a distance therebetween S, impact 91 is done at a position a suitable distance from the first receiver 93, the vertical displacement waveform detected shows evident arrival of the R waves. From the detected waveform, the times of arrival of the R waves at the two receivers 93, 94 are $T_{R1}$ and $T_{R2}$ respectively, thereby, the time period that the R waves propagated from the first receiver 93 to the second receiver 94 is $\Delta T_R = T_{R2} - T_{R1}$ then the speed of the R waves is obtained, i.e., $C_R = S/\Delta T_R$.

Step 2 (measuring speed of the P waves $C_P$): Before arrival of the R waves, there has been displacement disturbance induced by the arrival of the P waves; however, amplitude of vibration of it is smaller than that of the disturbance induced by the arrival of the R waves. If the front portion of the waveform thereof is partially amplified, the displacement response caused by the arrivals of the P waves at the first receiver 93 and the second receiver 94 respectively are $T_{P1}$ and $T_{P2}$. Similar to the step 1, the speed of the P waves is obtained, i.e., $C_P = S/T_{P2} - T_{P1}$.

Step 3 (determining $H_O$, $H_1$ and $H_2$): After the speed of the R waves and the speed of the P waves are obtained-, detecting of the crack is performed in site, $H_0$, $H_1$ and $H_2$ are given, the displacement waveform obtained by the first receiver 93 allocated at the same side of the source of impact shows the initiating time $t_1$ of downward disturbance induced by the arrival of the R waves; the second receiver 94 is allocated at the opposite side of the source of impact 91, the first arriving wave sensed by the second receiver 94 is a diffraction wave going around the tip of the crack, the waveform thereof shows the arrival time $t_2$ of the diffraction wave.

Step 4 (substituting in the formula (1) to obtain the value of $\Delta t$): Deriving from the formula (1), we get the time when an impact is done, and get the time period of propagation $\Delta t$ that the P waves arrive at the second receiver 94 diffracted via the tip of the crack. Step 5 (substituting in the formula (2) to obtain the value of the depth d): The time period of propagation and the speed of the P waves are substituted in the formula (2) to obtain the depth d of the crack.

Examples show that, although the time-of-flight diffraction technique leading in the source of waves by impact can accurately detect the depth of the crack on concrete, it has the following defects:

1. The R waves must be detected in the first place before derivation of the occurring time of the source of waves: Calculation for this is complicated, and can increase difficulty and variation in evaluation; thereby, efficiency of evaluation is lowered.
2. The technique can not be operated by only one person: When in operating, a person can not maintain the two receivers in positions simultaneously and has the sphere struck on a predetermined position accurately; normally an assistant is wanted, that is, the two persons shall operate together.
3. The technique requires a dual receiver; this makes higher complexity of equipment arrangement and cost.

SUMMARY OF THE INVENTION

The principal object of the present invention is to provide an evaluation method for concrete structures; it can conveniently and accurately detect the depth of a surface-opening crack in concrete. Another object of the present invention is to provide an evaluation method for concrete structures, wherein, the work of evaluation can be completed only with a single receiver; this not only reduces cost, but also simplifies the works of evaluation and signal analysis.

The present invention will be apparent after reading the detailed description of the preferred embodiment thereof in reference to the accompanying drawings, wherein:

BRIEF DESCRIPTION OF THE DRAWINGS

FIGS. 3A, B and C are views respectively showing the positions of the evaluation device of the present invention and the results obtained in the first test;

DETAILED DESCRIPTION OF THE PREFERRED EMBODIMENT

Figure 1:
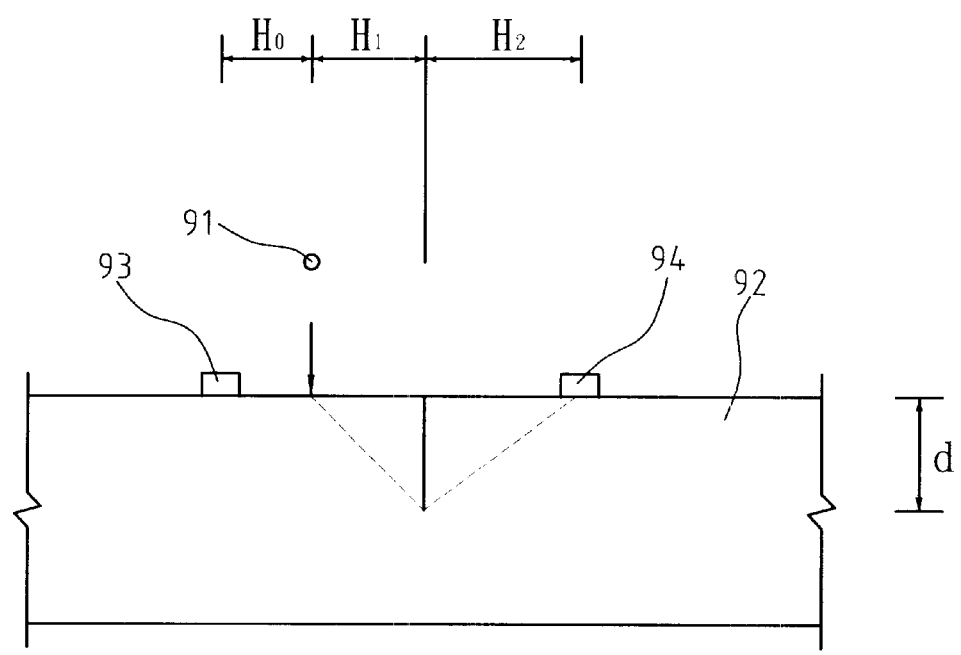
FIG. 1 is a schematic view showing the positions of an evaluation device for detecting cracks and two sensors used in the prior art.

Referring to FIGS. 2 A, B and C, the evaluation device of the present invention is composed mainly of a conductive impact device 10 a sensing film 14, a receiver 20, an operation device 30 and an auxiliary circuit 40. The detailed characteristics of the evaluation device are as follows:

1. The conductive impact device 10 is flexible and has a 10 cm long connecting section 11, and an impacting end 12 connecting with one end of the connecting section 11 and a knob 13 in opposition to the impacting end 12.
2. The sensing film 14 is soft and thin, and includes a conductive film 141 and a non-conductive plastic film 142 which is stuck at the point to be impacted. The conductive film 141 is connected with a third wire 16; when the conductive impact device 10 knocks down to contact the conductive film 141, a first wire 15 will be connected with the third wire 16 to form a closed circuit from an open circuit.
3. The receiver is used to receive the signals caused by arrivals of P waves, S waves and R waves, to transmit the signals of the waves out of a second wire 21. It is tested twice before crack evaluation, in order to calculate a penetration time r and speed of the P waves $C_P$.
4. The operation device 30 (such as a notebook computer) includes a data acquisition card 31 (analog/digital converter) to receive the signals from the first wire 15, the third wire 16 and the second wire 21. The operation device 30 can calculate the penetration time T and the speed of the P waves $C_P$ before the crack evaluation, then calculate the depth of the crack.
5. The auxiliary circuit 40 (as shown in FIG. 2 C) is connected to the first wire 15 and the third wire 16 parallelly connected with each other; the third wire 16 is serially connected with an electric power source 41 (such as a DC battery) and a closed circuit display element 43 (such as a lamp bulb or a buzzer for indicating the power on state). The first wire 15 and the third wire 16 are parallelly connected with an electric resistant 42 therebetween to form a closed circuit (loop), the signal of difference of voltage between the two ends of the resistant 42 is stably transmitted into the analog/digital interface card 31.

Figure 2A:
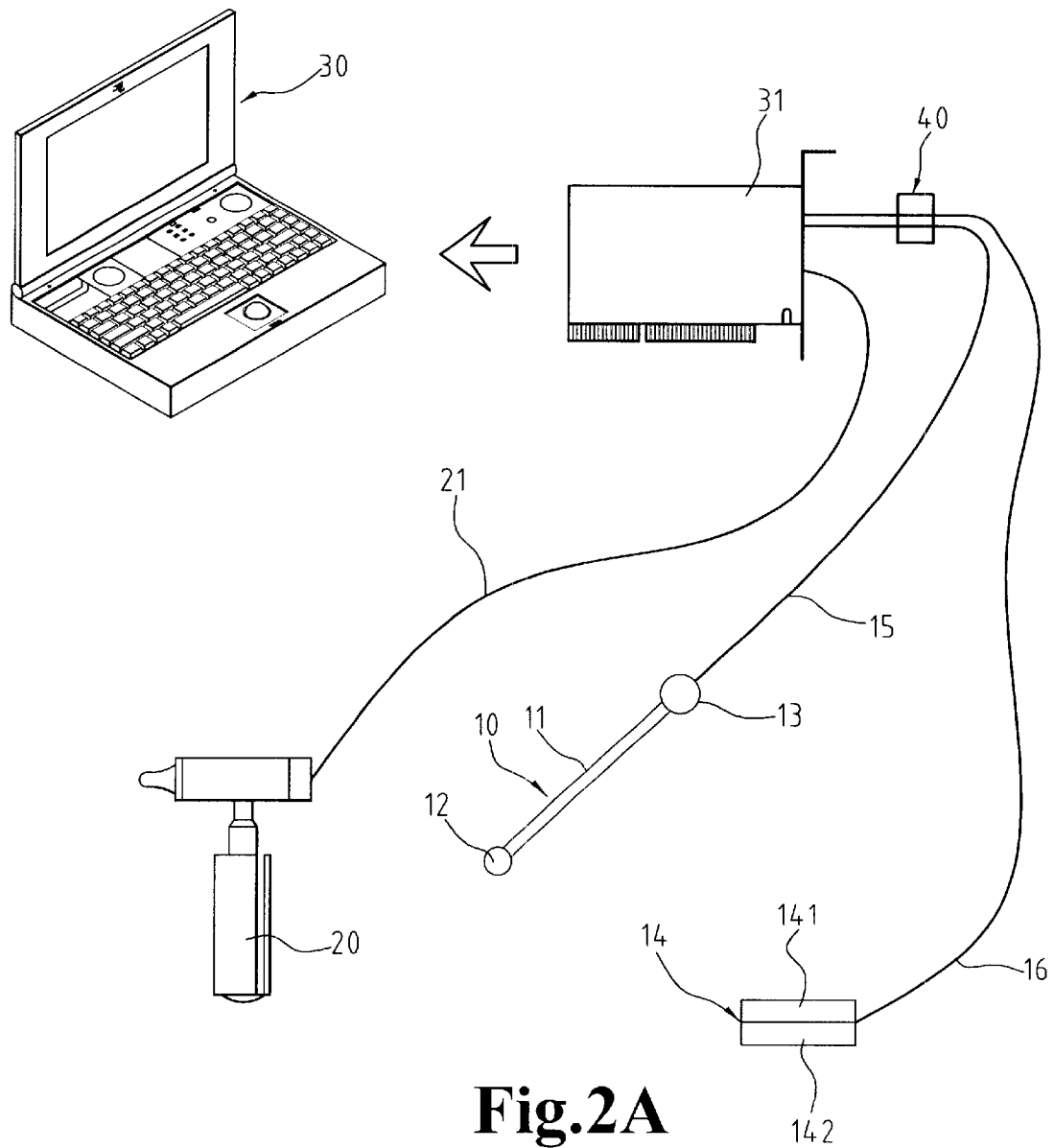
FIG. 2A is a schematic perspective view of the system of the present invention.
Figure 2B:
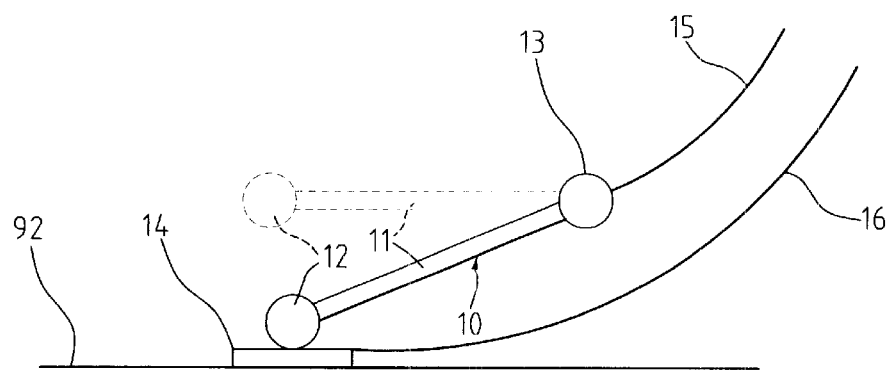
FIG. 2B is a schematic view of the impact device of the present invention.
Figure 2C:
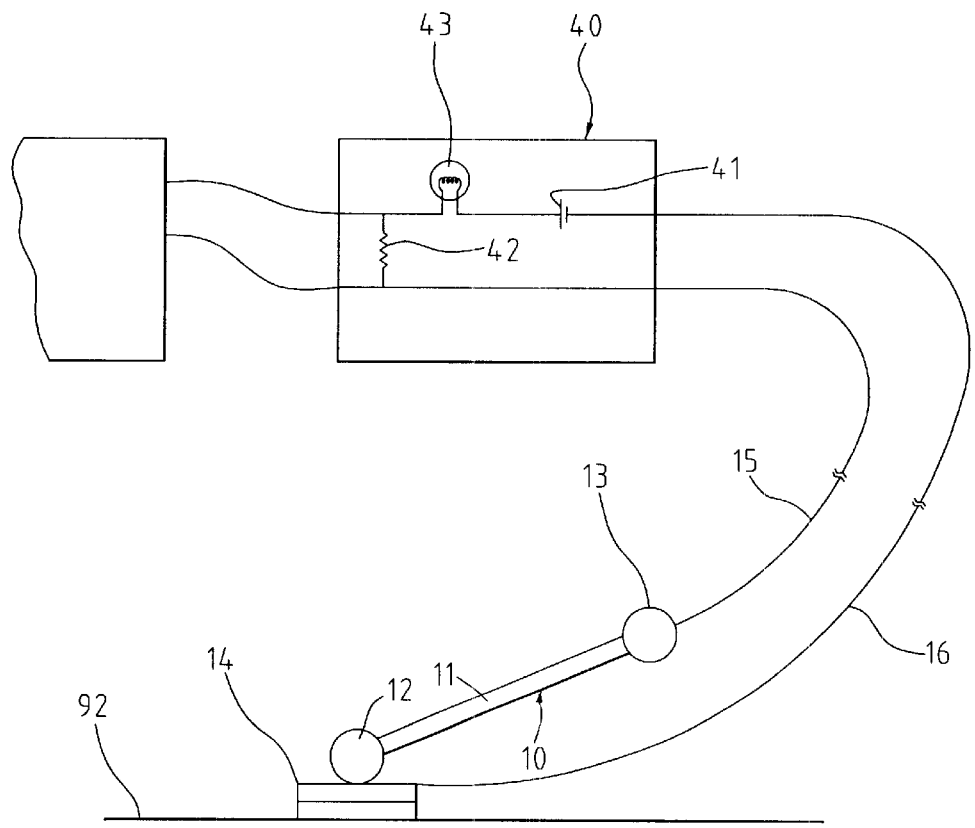
FIG. 2C is a schematic view showing an auxiliary circuit is used together with the impact device of the present invention.

The present invention provides the sensing film 14 sensitive to the occurring time of the source of sensible waves, together with the conductive impact device 10 of which the impact end is-made of a steel sphere with a diameter around 3–20 mm. The first wire 15 is connected to the auxiliary circuit 40 and then to the analog/digital interface card 31, such as is shown in FIGS. 2A to 2C. When the steel sphere on the impact end- impacts the surface of concrete 92, the impact end is pressed down to contact the sensing film 14, so that the conductive film 141 of the sensing film 14 form a conductive loop with the first wire 15 and the third wire 16 to generate signals of voltage. However, the impact end can only really contact the surface of concrete 92 when it is continued to be pressed down to extend through the conductive film 141 and the non-conductive plastic film 142, thereby, the actual initial time of steel sphere to start to contact with concrete is later than the time receiving the initial voltage signal. And the time difference -is called the penetration time τ.

The voltage signal is sent to the auxiliary circuit 40 via the first wire 15 and the third wire 16, and is transmitted to the analog/digital interface card 31, finally to the operation device 30. Thereby, the contact tine-history waveform induced when the steel sphere impacts the surface of concrete can be traced and recorded, and the occurring time of the source of waves can then be obtained.

Figure 4A:
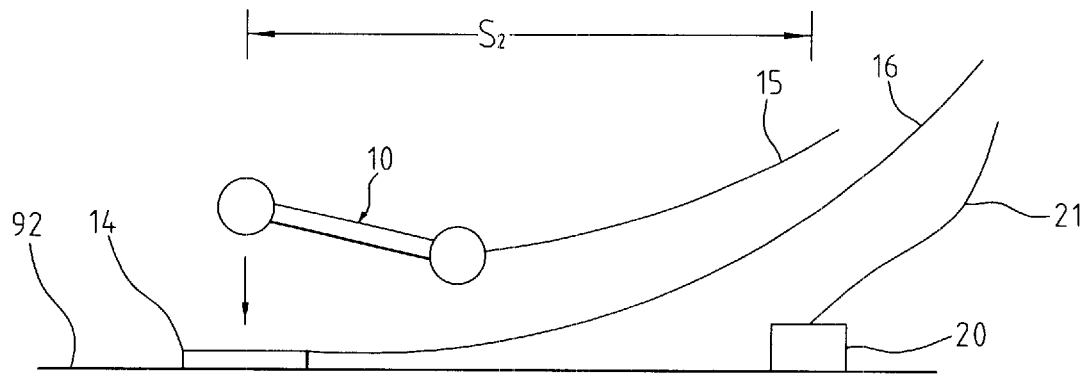
FIGS. 4A, B and C are views respectively showing the positions of the evaluation device of the present invention and the results obtained in the second test.
Figure 4B:
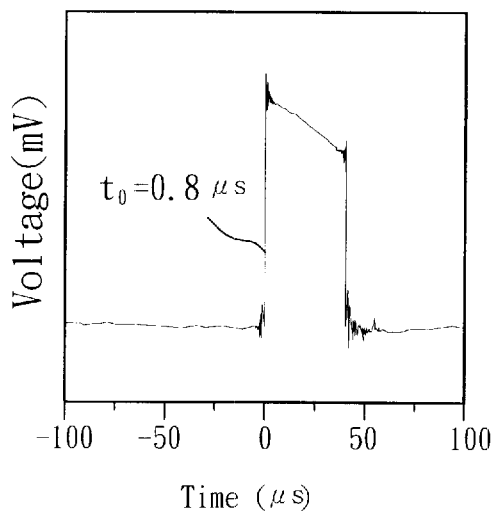
Figure 4C:
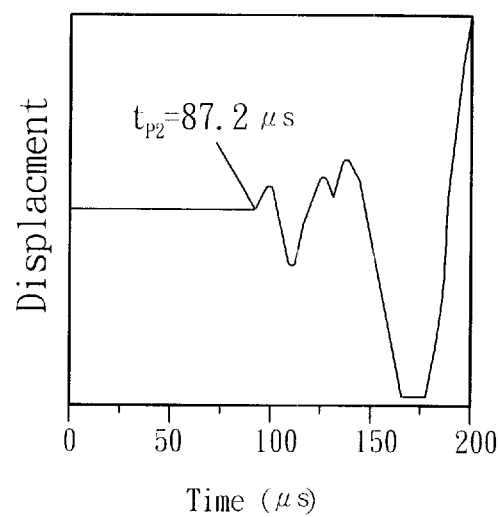
Figure 5A:
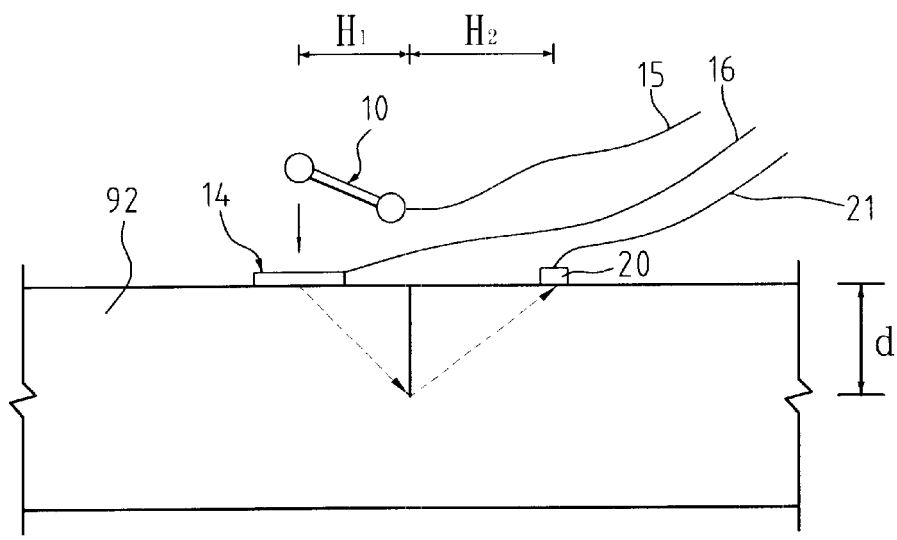
FIGS. 5A, B and C are views respectively showing the positions of the receivers of the present invention for detecting the crack and the results.

FIGS. 3 to 5 show an example of using the present invention to detect the depth of a surface-opening crack in concrete. They are only for illustration and not for giving any limitation to the scope of the present invention. The method of crack evaluation of the present invention including the following four steps (as shown in FIG. 6:

Step 1 (61) (detecting the penetration time τ and the speed of the P waves $C_P$): To determine the penetration time τ and the speed of the P waves $C_P$, it is required that a single receiver 20 performs two impact tests at different positions to get two sets of data for calculating the penetration time τ and the speed of the P waves $C_P$. FIGS. 3 and 4 give the results obtained from two tests. The first test is shown in FIG. 3A, the impacting sphere 12 is kept a distance 0.20 m from the receiver 20. FIG. 3B shows the recorded contact time-history waveform of steel sphere, FIG. 3C shows the waveform recorded by the receiver 20. The receiver 20 is then moved to a distance 0.30 m from the sphere (as shown in FIG. 4) to perform the second impact test. FIG. 4B shows the recorded contact time-history waveform of steel sphere, FIG. 4C shows the waveform recorded by the receiver 20. As shown in FIGS. 3B and 3C, during the first test, the time $T_{P_1}$ that the P waves arrive at the first test position of the receiver 20 is 62.0−1.0=61.0 microseconds. And as shown in FIGS. 4B and 4C, the time $T_{P_2}$ that the P waves arrive at the second test position of the receiver 20 is 87.2−0.8=86.4 microseconds.

According to: distance=the speed of the waves×time, we get:

For the first impact test: $0.2=C_P \times (61.0-\tau)$

For the second impact test: $0.3=C_P \times (86.4-\tau)$

With the two equations, we can get that the speed of the P waves $C_P$ is 3937 m/s, and the penetration time τ is 10.2 μs.

Step 2 (62) (determining $H_1$ and $H_2$): FIG. 5A shows an example using a steel sphere capable of recording the occurring time of the source of waves to detect the crack on the concrete. The impacting end, 12 is kept a distance ($H_1$) 0.15 m from the crack. The receiver 20 is allocated at the-other side a distance ($H_2$) 0.15 m from of the crack, the receiver 20 is used as the second receiver 94 in the prior art, the distance Ho and the first receiver 93 in the prior art are omitted here.

Figures 5B, 5C:
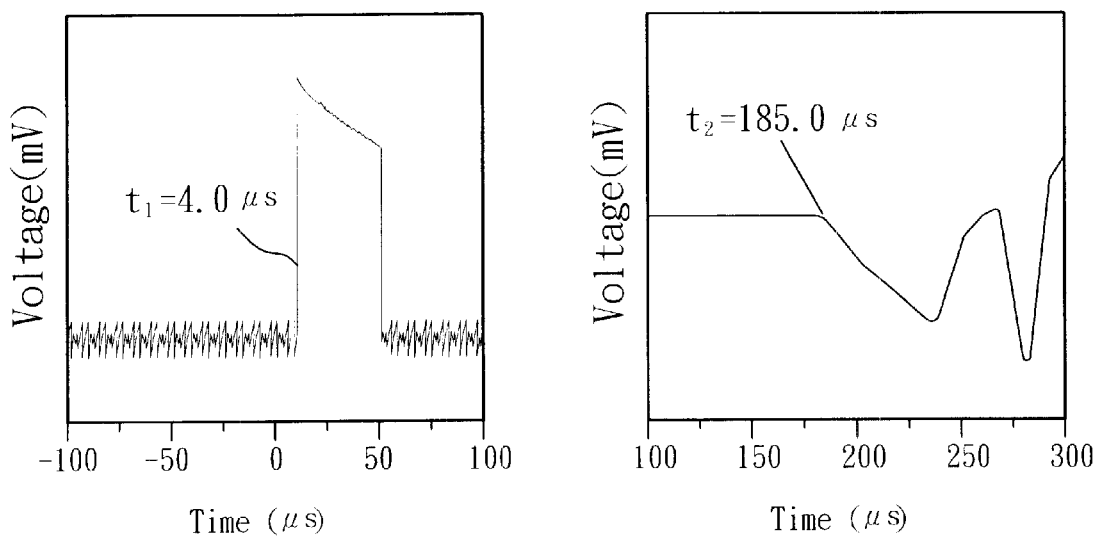
Figure 6:
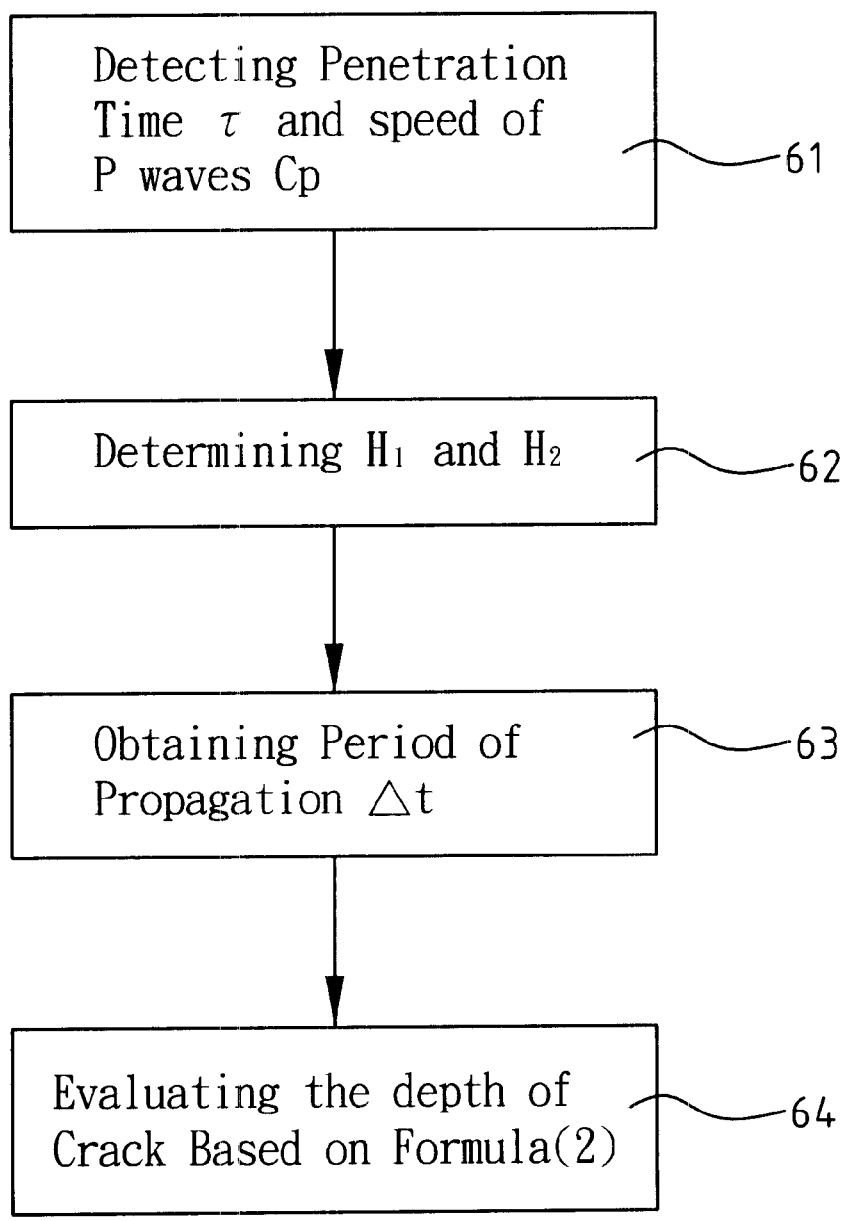
FIG. 6 shows a flow chart of the present invention in evaluating the crack.

Step 3 (63) (obtaining the time period of propagation Δt by means of the formula $\Delta t=t_2-t_1-\tau$): after impact, the contact time-history waveform of the impact of the sphere recorded and the waveform recorded by the receiver 20 are respectively depicted in FIGS. 5B and 5C. It has been known that the penetration time τ=10.2 μs, and the occurring time of the source of waves obtained from the transient reacting waveform induced by the impact in FIG. 5B is 4.0 μs ($t_1$), and the time period that the P diffraction waves arrive at the receiver 20 via the tip of the crack obtained from FIG. 5C is 185.0 μs ($t_2$); thereby, the time period that the P waves arrive at the second receiver 20 started from the source of impact and diffracted via the tip of the crack can be calculated from $\Delta t=t_{2-t1-\Delta}=185-4.0-10.2=170.8$ μs.

Step 4 (64) (substituting the above results in the formula (2) to obtain the value of the depth d): The time period of propagation and the speed of the P waves 3937 m/s obtained are substituted in the formula (2) to obtain the depth 0.3001 m of the crack. The value is very close to the real depth 0.30 m of the crack. This example shows that the initial time of impact can be obtained by deducting the penetration time τ from t1. Therefore, as is shown in FIG. 6, only four steps are required to obtain the object of crack evaluation on concrete.

The key point of the evaluation method and the evaluation device of the present invention resides in deduction of the penetration time τ when in application to evaluation of cracks in concrete. Wherein, the sensing film (such as the products of U.S. 3M company) is cheap and can be obtained conveniently, no order for the goods is necessary. It only needs to use a single receiver to be operated by only one person, and it is no necessity to derive the occurring time of the source of waves from the speed of the R waves. Cost of the hardware and software for the present invention is low, and the steps for evaluation thereof is simple; the present invention is substantially contributive to the quality evaluation of concrete.

The above statement is only for illustrating a preferred embodiment of the present invention. It will be apparent to those skilled in this art that all equivalent modifications and changes without departing from the spirit and features of the present invention shall fall within the scope of the appended claims. Having now particularly described and ascertained the nature of the invention and in what manner the same is to be performed, we declare that

What we claim is:

1. An apparatus for detecting quality of concrete structures, comprising:

a conductive impact device including a connecting section with a predetermined length, said connecting section having one end formed with an impacting end and the other end formed with a knob;

a sensing film including a conductive film and a non-conductive plastic film stuck at a point to be impacted;

a receiver for receiving signals introduced by longitudinal waves, transverse waves and Raleigh's waves;

an operation device including an analog-to-digital interface card for receiving signals from a first wire connected to said connecting section, a second wire connected to said receiver, and a third wire connected to said conductive film for calculating the depth of a crack; and an auxiliary circuit including a resistant connected between said first and third wires, and an electric power source connected in serial with said third wire;

wherein when said conductive impact device is in contact with said conductive film, said first wire is connected with said third wire through said connecting section to form a closed circuit from an open circuit.

2. The apparatus for detecting quality of concrete structures as in claim 1, wherein said impacting end is made of a steel sphere with a diameter around 3–20 mm and is adapted for generating a source of waves for evaluation.

3. The apparatus for detecting quality of concrete structures as in claim 1, wherein said connecting section of said impact device is made of a flexible material.

4. A method for detecting quality of concrete structures, comprising the steps of:

preparing a receiver and performing two impact tests at different positions to get two sets of data for calculating a penetration time $\tau$ and speed of longitudinal P waves ($C_P$);

performing an evaluation test at an impact point and determining a first distance $H_1$ between said impact point and a crack and a second distance $H_2$ between said impact point and the receiver;

measuring an occurring time $t_1$ of a source of waves from a transient reacting waveform induced by said evaluation test, and a time $t_2$ of the arrival of P diffraction waves at the receiver via a tip of said cracl;

obtaining a value of $\Delta t$ after impact by means of a formula $\Delta t = t_2 - t_1 - \tau$; and substituting $C_P$, $\Delta t$, $H_1$ and $H_2$ in the following formula to obtain the value of depth d of said crack, $$d = \sqrt{\left[\frac{(C_P \times \Delta t)^2 + H_1^2 - H_2^2}{2 \times C_P \times \Delta t}\right]^2 - H_1^2}.$$

* * * * *